(12) United States Patent
Masuda

(10) Patent No.: US 7,940,397 B2
(45) Date of Patent: May 10, 2011

(54) OPTICAL CONNECTOR AND AN OPTICAL TOMOGRAPHIC IMAGING SYSTEM USING THE SAME

(75) Inventor: Tadashi Masuda, Ashigara-kami-gun (JP)

(73) Assignee: FUJIFILM Corporation, Tokyo (JP)

(*) Notice: Subject to any disclaimer, the term of this patent is extended or adjusted under 35 U.S.C. 154(b) by 219 days.

(21) Appl. No.: 12/324,341

(22) Filed: Nov. 26, 2008

(65) Prior Publication Data

US 2009/0135429 A1 May 28, 2009

(30) Foreign Application Priority Data

Nov. 28, 2007 (JP) ................................. 2007-307553

(51) Int. Cl.
G01B 9/02 (2006.01)

(52) U.S. Cl. ........................................................ 356/479

(58) Field of Classification Search .................. 356/477, 356/479, 497
See application file for complete search history.

(56) References Cited

U.S. PATENT DOCUMENTS

| | | | |
|---|---|---|---|
| 5,101,807 A | 4/1992 | Kawashima | |
| 6,010,251 A * | 1/2000 | Koyanagi et al. | 385/93 |
| 6,445,939 B1 * | 9/2002 | Swanson et al. | 600/342 |
| 6,485,413 B1 * | 11/2002 | Boppart et al. | 600/160 |
| 6,615,072 B1 * | 9/2003 | Izatt et al. | 600/478 |
| 6,907,163 B2 * | 6/2005 | Lewis | 385/33 |
| 7,367,716 B2 * | 5/2008 | Nagano et al. | 385/89 |
| 7,371,013 B2 * | 5/2008 | Nagano et al. | 385/89 |
| 7,466,017 B2 * | 12/2008 | Yoshida et al. | 257/678 |
| 7,474,822 B2 * | 1/2009 | Kobayashi et al. | 385/35 |
| 2002/0033941 A1 * | 3/2002 | Seward | 356/153 |
| 2003/0044115 A1 * | 3/2003 | Lewis | 385/33 |
| 2004/0027690 A1 * | 2/2004 | Takahashi | 359/726 |
| 2004/0081397 A1 * | 4/2004 | Liu | 385/34 |
| 2004/0184726 A1 * | 9/2004 | Miao et al. | 385/33 |
| 2004/0184728 A1 * | 9/2004 | Miao et al. | 385/33 |
| 2004/0208422 A1 * | 10/2004 | Hagood et al. | 385/16 |
| 2005/0030840 A1 * | 2/2005 | Hagood et al. | 369/44.14 |
| 2005/0168751 A1 | 8/2005 | Horii et al. | |
| 2006/0215966 A1 * | 9/2006 | Nagano et al. | 385/88 |

(Continued)

FOREIGN PATENT DOCUMENTS

| | | |
|---|---|---|
| DE | 28 41 720 A1 * | 4/1980 |
| EP | 0 348 117 A2 * | 12/1989 |
| EP | 0 357 132 A2 * | 3/1990 |

(Continued)

OTHER PUBLICATIONS

EP Communication, dated Mar. 4, 2009, issued in corresponding EP Application No. 08020644.4, 8 pages.*

(Continued)

*Primary Examiner* — Patrick J Connolly
(74) *Attorney, Agent, or Firm* — Sughrue Mion, PLLC

(57) ABSTRACT

The optical connector includes a holder unit, a first optical fiber fixedly supported by the holder unit and having an inclined end face, a first collimating lens spaced from the inclined end face, a mounting unit supported relative to the holder unit, a second optical fiber disposed opposite the first collimating lens and having an inclined end face, a second collimating lens disposed between the first collimating lens and the second optical fiber and spaced from the inclined end face of the second optical fiber, wherein an optical transmission system comprising the first optical fiber and the first collimating lens is symmetric to an optical transmission system comprising the second optical fiber and the second collimating lens with respect to a plane perpendicular to the optical axis.

6 Claims, 5 Drawing Sheets

U.S. PATENT DOCUMENTS

| | | | |
|---|---|---|---|
| 2006/0215967 A1* | 9/2006 | Nagano et al. | 385/88 |
| 2006/0219879 A1* | 10/2006 | Katou et al. | 250/227.21 |
| 2006/0239317 A1* | 10/2006 | Yoshida et al. | 372/36 |
| 2006/0239611 A1* | 10/2006 | Tanaka et al. | 385/33 |
| 2006/0256446 A1* | 11/2006 | Tanaka et al. | 359/641 |
| 2007/0211999 A1* | 9/2007 | Kobayashi et al. | 385/79 |
| 2008/0080812 A1* | 4/2008 | Kobayashi et al. | 385/35 |
| 2009/0135429 A1* | 5/2009 | Masuda | 356/477 |
| 2009/0244545 A1* | 10/2009 | Toida | 356/477 |
| 2009/0251704 A1* | 10/2009 | Masuda | 356/477 |

FOREIGN PATENT DOCUMENTS

| | | | |
|---|---|---|---|
| EP | 1 406 100 A2 * | 4/2004 | |
| JP | 2000-131222 A | 5/2000 | |
| JP | 2005-037731 A * | 2/2005 | |

OTHER PUBLICATIONS

Communication pursuant to Article 94(3) EPC, dated Jan. 12, 2011, issued in corresponding EP Application No. 08 020 644.4, 5 pages.

* cited by examiner

US 7,940,397 B2

OPTICAL CONNECTOR AND AN OPTICAL TOMOGRAPHIC IMAGING SYSTEM USING THE SAME

The entire contents of the literature cited in this specification are incorporated herein by reference.

BACKGROUND OF THE INVENTION

The invention relates to an optical connector for guiding light from one optical fiber to another optical fiber and an optical tomographic imaging system using the optical connector and more particularly to an optical connector achieving a noncontact connection between light guiding optical fibers to guide light from one optical fiber to another optical fiber and an optical tomographic imaging system for irradiating an object to be measured with light to acquire an optical tomographic image from returning light reflected by the object under measurement.

Acquisition of a cross-sectional image of a sample under measurement such as biological tissue without cutting thereinto may be achieved using an optical tomographic imaging system employing optical coherence tomography (OCT) measuring.

The OCT measuring is a kind of optical interferometric measurement using the optical interference that occurs only when the optical path lengths of the measuring light and the reference light, into which the light from the light source is divided, are matched to within the coherence length of the light from the light source.

An optical tomographic imaging system using the OCT measuring is disclosed, for example, in JP 2000-131222 A, which comprises a light source; a first optical coupler for splitting the light emitted from the light source into measuring light and reference light; an optical scan probe including a measuring unit for irradiating the sample under test or the object under measurement with the measuring light and detecting the light reflected and returned therefrom, an optical fiber for transmitting the measuring light and the returning light, and a transparent sheath covering the optical fiber and the measuring unit; and a second coupler fox causing the reference light to interfere with the returning light both guided along the same optical path length as the measuring light; and an optical tomography system including a computing unit for detecting a tomographic image from the results of interference. With the optical tomographic imaging system disclosed in JP 2000-131222 A, which has the optical fiber in the measuring unit rotatably connected to an optical rotary joint, the measuring unit located close to the tip of the optical scan probe is inserted up to a position to be measured and rotated by turning the optical fiber to acquire a plurality of tomographic images of the object under measurement with its rotating measuring unit, thus reconstructing a two-dimensional sectional image.

The optical fibers for guiding returning light and reference light in the optical tomographic imaging system are formed by a plurality of optical fibers. The optical fibers (e.g., an optical fiber from a light source and an optical fiber from an optical coupler or an optical fiber from an optical coupler and an optical fiber from an optical probe) are optically connected by an optical connector. The optical connector places the end faces of optical fibers in contact to establish connection, ensuring light guiding with a high transmission efficiency.

SUMMARY OF THE INVENTION

An optical connector ensures light guiding with an increased transmission efficiency when the end faces of the optical fibers are placed into a close contact leaving no space therebetween. In particular, an optical connector of APC type that connects optical fibers each having an end face inclined by a given angle is capable of reducing attenuation of light (or return loss) that is caused by reflection of light on the contact surfaces of the optical fibers.

While the transmission efficiency may be increased with an optical connector whereby the end faces of optical fibers are placed in contact or in close contact with each other, problems are posed that returning light from the object under measurement attenuates as light is reflected or refracted at the opposite end faces of two optical fibers or the signal-to-noise ratio decreases as light reflected by the end faces of the optical fibers is guided to a detector along with the returning light. In the optical tomographic imaging system in particular, the ratio of the amount of returning light from the object under measurement to the amount of the measuring light, i.e., (amount of returning light)/(amount of measuring light), should be at least about 10-6 to 10-10 after the measuring light attenuates at the opposite end faces of both optical fibers. Accordingly, the attenuation of the returning light and the decrease of the signal-to-noise ratio thereof occurring at the opposite ends of the connected optical fibers as light is reflected at the end faces of the optical fibers are a matter of great importance. Further, with a small amount of the returning light in relation to the measuring light, the signal-to-noise ratio decreases when light reflected by the end faces of the optical fibers other than the returning light is guided to the detector along with the returning light.

It is true that the return loss can be held to a lower level when, as described above, an optical connector of APC type is used as an optical connector than when another type of optical connector is used. However, since, with an optical tomographic imaging system, the amount of returning light is small in relation to the amount of measuring light as described above, the signal-to-noise ratio decreases because of return loss and other causes even when an optical connector of APC type is used.

There is another problem that when attaching or detaching an optical fiber to replace an optical fiber or a light source or to perform other task, the tip of the optical fiber can be damaged or broken as the optical fibers contact each other.

A first object of the invention is to eliminate the above problems associated with the prior art and provide an optical connector capable of preventing decrease of the signal-to-noise ratio caused by reflection of light by the two opposite end faces of two connected optical fibers.

A second object of the invention is to provide an optical connector capable of detachably connecting light guiding optical fibers, preventing damage or break of the tips of the two connected optical fibers when detaching and attaching them, and preventing decrease of signal-to-noise ratio caused by reflection of light by the two opposite end faces of two connected optical fibers.

A third object of the invention is to provide an optical tomographic imaging system capable of efficiently acquiring a high-resolution optical tomographic image of an object under measurement by using the optical connector capable of achieving said first object.

A first aspect of the invention to achieve the above first object is to provide an optical connector used in an optical tomographic imaging system for acquiring an optical tomographic image of an object under measurement, the optical connector comprising: a holder unit; a first optical fiber fixedly supported by the holder unit and having on one end thereof an end face inclined a given angle with respect to a plane perpendicular to its optical axis; a first collimating lens disposed at a given distance from the inclined end face of the first optical fiber; a mounting unit supported with respect to the holder unit; a second optical fiber fixedly attached to the mounting unit, disposed opposite the first collimating lens, and having an end face inclined a given angle with respect to a plane perpendicular to its optical axis; and a second collimating lens fixedly attached to the mounting unit and disposed between the first collimating lens and the second optical fiber with a given distance from the inclined end face of the second optical fiber; wherein an optical transmission system comprising the first optical fiber and the first collimating lens is disposed symmetric to an optical transmission system comprising the second optical fiber and the second collimating lens with respect to a plane perpendicular to an optical axis.

Preferably, the first optical fiber and the second optical fiber are supported by respective ferrules and the ferrules have inclined end faces forming same planes as the inclined end faces of the first optical fiber and the second optical fiber, respectively.

Preferably, the mounting unit fixedly supporting the second optical fiber and the second collimating lens is detachable from the holder unit fixedly supporting the first optical fiber and the first collimating lens.

Preferably, the holder unit has a cylindrical projection of which an outer periphery has a tapered shape growing smaller in diameter toward a forward end thereof, and the mounting unit has a cylindrical bore having a tapered inner periphery in contact with the outer periphery of the projection such that the bore of the mounting unit engages with the projection of the holder unit to support the mounting unit with respect to the holder unit.

Preferably, the optical connector further comprises a positioning mechanism for fixing a position of the mounting unit with respect to the holder unit in a circumferential direction about an optical axis and fixing a relative position of the inclined end faces of the first optical fiber and the second optical fiber in a circumferential direction about an optical axis.

Preferably, the positioning mechanism comprises a key and a key groove that is formed in at least one of the holder unit and the mounting unit.

A second aspect of the invention to achieve the above third object is to provide an optical tomographic imaging system comprising: a light source; a splitter for splitting light emitted from the light source into measuring light and reference light; an optical probe for guiding the measuring light to an object under measurement and guiding returning light from the object under measurement, the optical probe having a measuring unit disposed at a tip thereof for radiating the measuring light to the object under measurement and detecting the returning light; a rotary drive unit for rotating the measuring unit of the optical probe; a combiner for combining the returning light detected by the measuring unit of the optical probe with the reference light to generate interference light; an interference light detector for detecting the interference light as interference signal; a tomographic information generator for acquiring a tomographic image from the interference signal detected by the interference light detector; and a plurality of connecting units for optically connecting the light source and the splitter, the splitter and the rotary drive unit, the rotary drive unit and the combiner, and the combiner and the interference light detector, respectively; wherein at least one of the connecting units comprises a plurality of optical fibers and an optical connector of claim 1 for establishing a connection between one optical fiber with another optical fiber.

Preferably, the light source emits light with a wavelength thereof swept with a constant period.

The first aspect of the invention directed to the optical connector prevents light reflected by the two opposite end faces of the two connected optical fibers from combining with the returning light and prevents attenuation of guided light, in particular the returning light from an object under measurement or decrease of the signal-to-noise ratio thereof.

It is also made possible to achieve a detachable, noncontact connection between optical fibers and prevent damage or break of the tips of the two connected optical fibers when attaching or detaching an optical fiber.

The second aspect of the invention directed to the optical tomographic imaging system achieves efficient acquisition of a high-resolution tomographic image of an object under measurement by using the optical connector according to the first aspect capable of producing the above effects.

BRIEF DESCRIPTION OF THE DRAWINGS

These and other objects, features, and advantages of the present invention will be apparent from the following detailed description and accompanying drawings in which.

DETAILED DESCRIPTION OF THE INVENTION

Now, the inventive optical connector and the optical tomographic imaging system using the same will be described in detail referring to the embodiments illustrated in the attached drawings.

Figure 1:
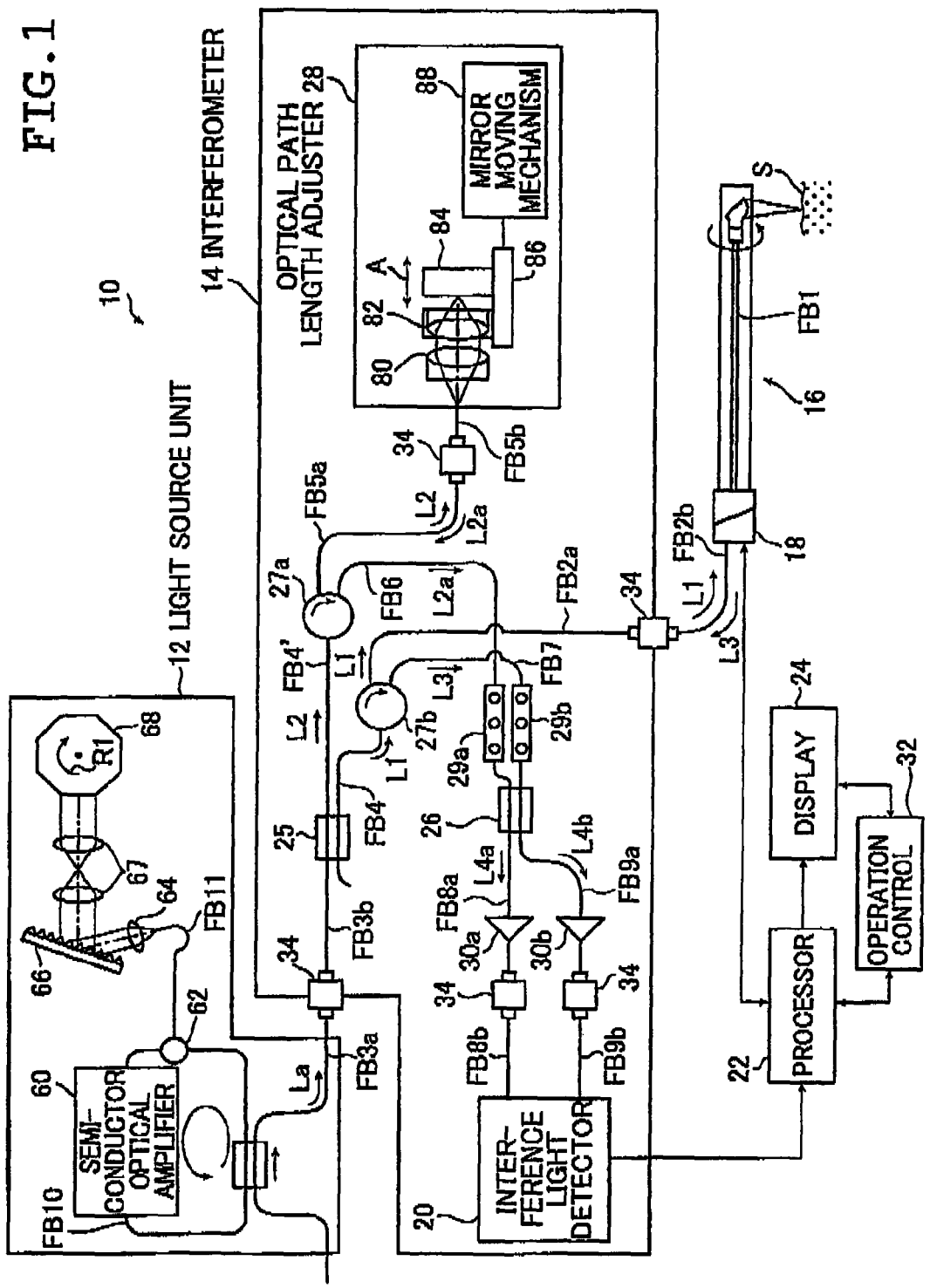
FIG. 1 is a block diagram schematically illustrating a configuration of an embodiment of the inventive optical tomographic imaging system using the inventive optical connector.

FIG. 1 is a block diagram illustrating a schematic configuration of an embodiment of the inventive optical tomographic imaging system using the inventive optical connector.

An optical tomographic imaging system 10 according to the invention illustrated in FIG. 1 acquires a tomographic image of an object under measurement by a measuring method based upon optical coherence tomography or OCT. The optical tomographic imaging system 10 comprises: a light source unit 12 for emitting light La; an interferometer 14 including a splitter 25 for splitting the light La emitted by the light source unit 12 into measuring light L1 and reference light L2, a combiner 26 for combining returning light L3 from an object under measurement or a sample under test and reference light L2a to produce interference light L4a, L4b, and an interference light detector 20 for detecting interference signal based upon the interference light L4a, L4b produced by the combiner 26; an optical probe 16 including a rotary optical fiber FB1 for guiding the measuring light L1 split by the splitter 25 of the interferometer 14 to the object under measurement and for guiding the returning light L3 from the object under measurement; a rotary drive unit 18 for rotating the rotary optical fiber FB1 while rotatably connecting the rotary optical fiber FB1 to a stationary optical fiber FB2 and transmitting the measuring light L1 and the returning light L3, the stationary optical fiber FB2 guiding the measuring light L1 to the rotary optical fiber FB1 and guiding the returning light L3 guided by the rotary optical fiber FB1; a processor 22 for processing the interference signal detected by the interference light detector 20 of the interferometer 14 to acquire an optical tomographic image (also referred to simply as "tomographic image" below); a display 24 for displaying the tomographic image acquired by the processor 22; and an operation control 32 for entering conditions in the processor 22 and the display 24 and changing settings of the conditions, and performing other operations.

In addition to the splitter 25, the combiner 26, and the interference light detector 20, the interferometer 14 of the optical tomographic imaging system 10 comprises a circulator 27a for guiding the reference light L2 guided from the splitter 25 to an optical path length adjustor 28 and guiding the reference light L2a guided from the optical path length adjustor 28 to a polarization controller 23a, a circulator 27b for guiding the reference light L1 guided from the splitter 25 to the rotary drive unit 18 and guiding the returning light L3 to a polarization controller 29b, the optical path length adjustor 28 for adjusting the optical path of the reference light L2, the polarization controller 29a for rotating the polarization direction of the reference light L2a and the polarization controller 29b for rotating the polarization direction of the returning light L3, and a detector 30a for detecting the interference light L4a and a detector 30b for detecting the interference light L4b.

In the optical tomographic imaging system illustrated in FIG. 1, various optical fibers FB (FB3, FB4, FB5, FB6, FB7, FB8, FB9, etc.) are used including the rotary optical fiber FB1 and the stationary optical FB2 to provide optical paths for guiding and transmitting light including the emitted light La, the measuring light L1, the reference light L2 and the returning light L3 described above between the components such as optical devices.

The optical fiber FB2 connecting the interferometer 14 (specifically, the circulator 27b) and the rotary drive unit 18 is formed by an optical fiber FB2a from the interferometer 14 and an optical fiber FB2b from the rotary drive unit 18; the optical fiber FB2a and the optical fiber FB2b are connected by an inventive optical connector 34.

Likewise, the optical fiber FB3 connecting the light source 12 and the interferometer 14 (specifically, the splitter 25) is formed by an optical fiber FB3a from the light source 12 and an optical fiber FB3b from the interferometer 14; the optical fiber FB3a and the optical fiber FB3b are connected by an inventive optical connector 34.

The optical fiber FB5 connecting the circulator 27a and the optical path length adjustor 28, the optical fibers FB8 and FB9 connecting the combiner 26 and the interference light detector 20 in the interferometer 14 are formed by optical fibers FB5a, FB5b, FB8a, FB8b, FB9a, and FB9bFB, respectively, and connected by optical connectors 34 of the invention.

First, the optical connector 34 of the invention used for the optical tomographic imaging system 10 illustrated in FIG. 1 will be described.

Figure 2:
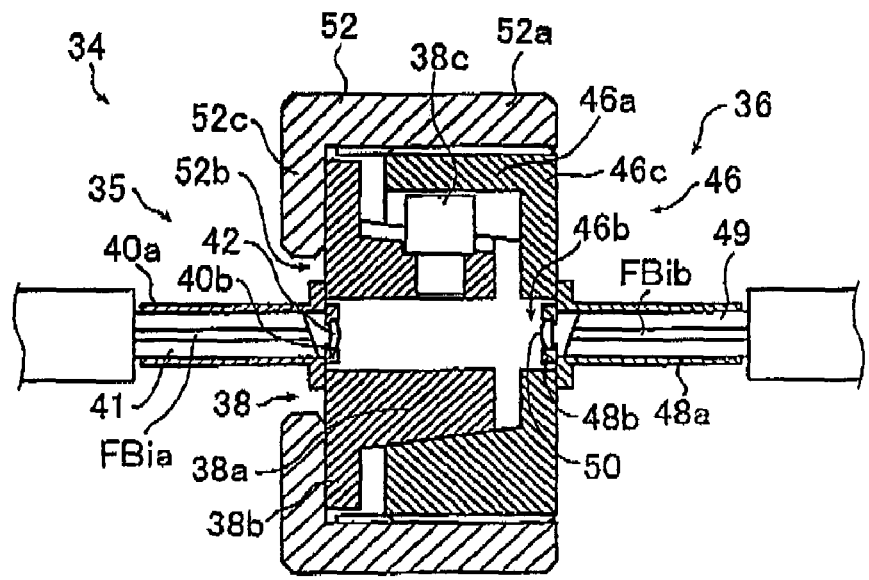
FIG. 2 is a schematic sectional view of an embodiment of the optical connector illustrated in FIG. 1.
Figure 3:
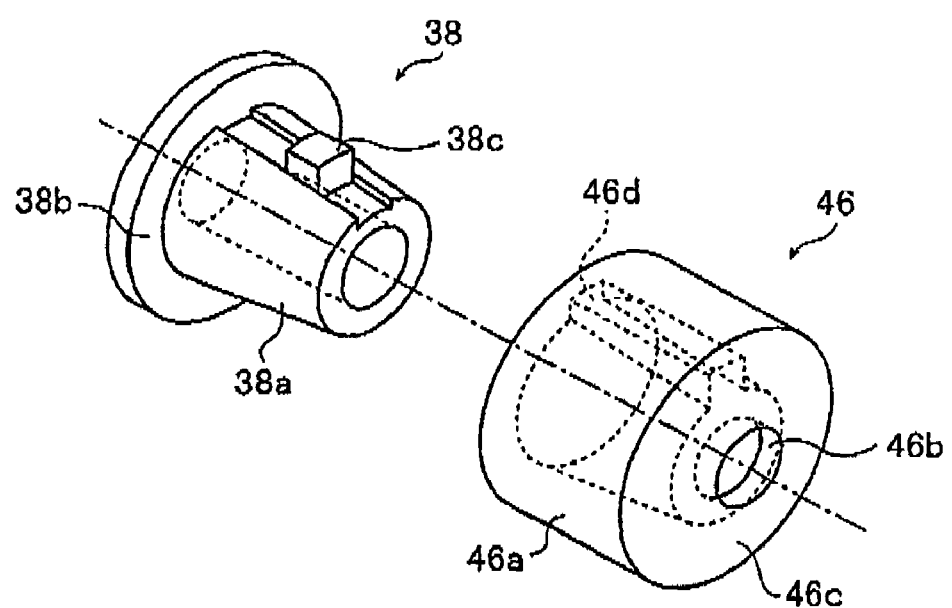
FIG. 3 is a schematic perspective view illustrating enlarged a male connector and a female connector of the optical connector of FIG. 2.
Figure 4:
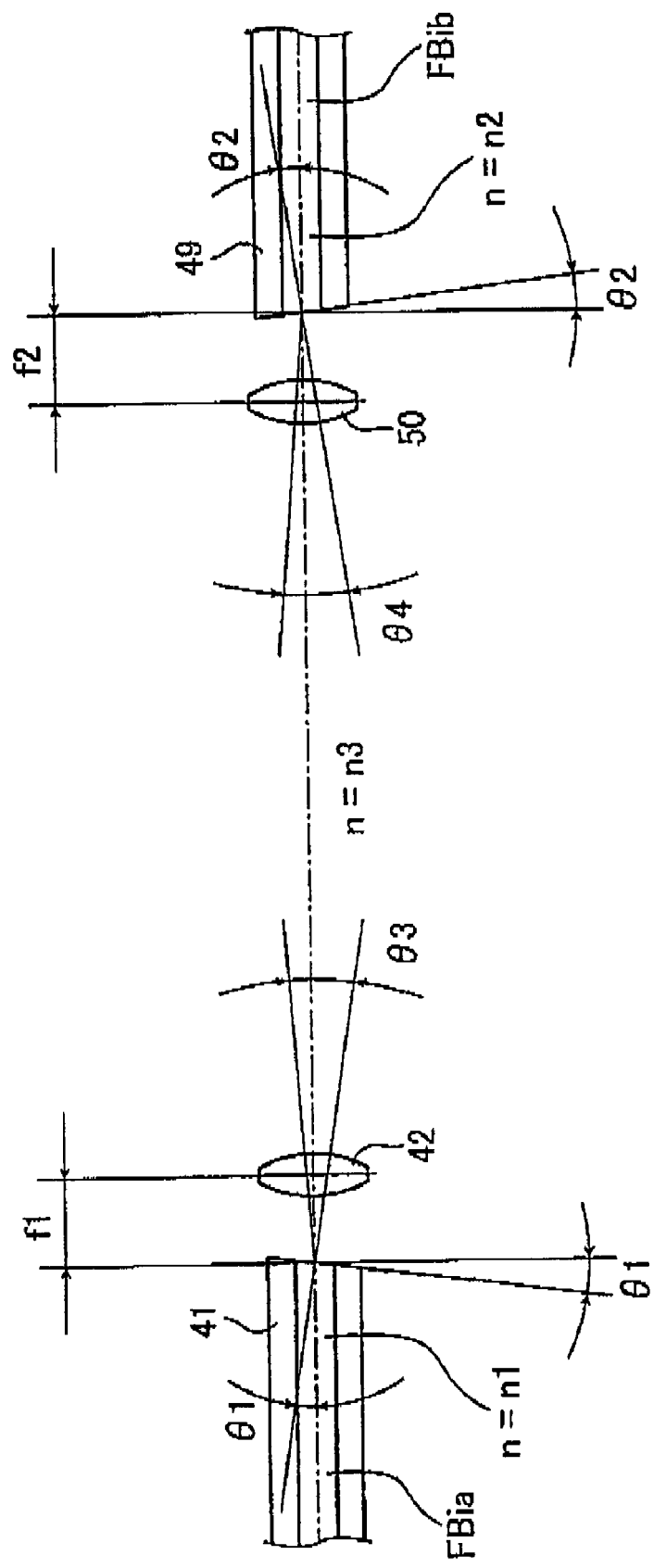
FIG. 4 is a view for explaining an example of the positional relationship of the optical fibers and the collimating lenses with respect to the optical connector illustrated in FIG. 2.

FIG. 2 is a schematic sectional view of the inventive optical connector illustrated in FIG. 1; FIG. 3 is a schematic perspective view illustrating enlarged a male connector and a female connector of the optical connector of FIG. 2; FIG. 4 is a view for explaining an example of the positional relationship of the optical fibers and the collimating lenses with respect to the optical connector illustrated in FIG. 2.

The optical connector 34 illustrated in FIG. 2 comprises a holder unit 35 comprising a male connector 38 and holders 40a, 40b fixedly mounted to one end face of the male connector 38, an optical fiber FBia (i=2, 3, 5, 8 and 9) secured with the holder 40a, a collimating lens 42 secured with the holder 40b, a mounting unit 36 comprising a female connector 46 supported by the male connector 38 and holders 48a, 48b fixedly mounted to substantially the center of one end face of the female connector 46, an optical fiber FBib (i=2, 3, 5, 8 and 9) secured with the holder 48a, a collimating lens 50 secured with the holder 48b, a fastener screw 52 for fastening the male connector 38 and the female connector 48.

The holder unit 35 is a member comprising the male connector 38 and the holders 40a, 40b and provided to hold the optical fiber FBia and the collimating lens 42 in a given position and support the female connector 46 of the mounting unit 36.

As illustrated in FIGS. 2 and 3, the male connector 38 has a cylindrical projection 38a of which the outer periphery grows smaller in diameter toward the mounting unit 36 and of which the inner periphery has a constant diameter and a flange 38b formed on the outer periphery at the base (i.e., the end face opposite from that closer to the mounting unit 36) of the projection 38a.

The outer periphery of the projection 38a of the male connector 38 has a groove formed in a part thereof where a screw 38c is disposed to provide a positioning mechanism engaging with the female connector to be described.

The holder 40a is a flanged circular tubing member for holding centrally therein the optical fiber FBia held by a cylindrical ferrule 41. The optical fiber FBia held by the ferrule 41 is held by the holder 40a such that its end face is spaced a given distance from the flanged end face of the holder 40a. The holder 40a is attached, directed outwardly, to the external periphery of the central aperture of the flange 38b of the male connector 38 such that the central optical axis of the optical fiber FBia held by the holder 40a is located substantially at the center of the circular central aperture of the male connector 38.

The ferrule 41 has the optical fiber FBia inserted therein to hold and protect the optical fiber FBia and may typically be a zirconia ferrule or a metal ferrule formed of a metal such as nickel alloy.

The holder 40b is a flanged circular tubing member for holding the collimating lens 42 and its flange section is attached to the flange section of the holder 40a such that the center of the end face of the optical fiber FBia and the center of the collimating lens 42 are spaced from each other on the optical axis thereof by a given distance, specifically by the focal distance of the collimating lens 42.

The central axis of the optical fiber FBia and the center of the collimating lens 42 are offset from each other to permit horizontal emission of light.

The optical fiber FBia transmits guided light to the optical fiber FBib and, depending upon the position in which the optical connector 34 is disposed, transmits light guided by the optical fiber FBib. The end face of the optical fiber FBia and the end face of the ferrule 41 having the optical fiber FBia inserted therein at the core are inclined end faces forming an identical plane inclined a given angle with respect to the plane perpendicular to the central axis of the optical fiber FBia.

The collimating lens 42 collimates the light emitted from the end of the optical fiber FBia and allows the collimated light to enter the collimating lens 50 and, depending upon the position in which the optical connector 34 is disposed, focuses the collimated light from the collimating lens 50, allowing the thus focused light to enter the optical fiber FBia also. The end face of the optical fiber FBia and the collimating lens 42 are positioned such that the center of the inclined end face of the optical fiber FBia and the center of the collimating lens 42 are spaced from each other on the optical axis thereof by a distance equal to the focal distance of the collimating lens 42.

The mounting unit 36 comprises the female connector 46 and the holders 48*a*, 48*b*. The mounting unit 36 is a member for supporting the optical fiber FBib and the collimating lens 50 held substantially at the center of the inside of the female connector 46 such that the female connector 46 located on the forward end of the mounting unit 36 is fitted onto the projection 38*a* of the male connector 38 and supported by the holder unit 35.

As illustrated in FIGS. 2 and 3, the female connector 46 comprises a circular tubing section 46*a* opening on one end thereof and a discal section 46*c* having a central aperture 46*b* at the opposite end. The inner periphery of the circular tubing section 46*a* has a tapered shape contouring the outer periphery of the projection 38*a* of the male connector 38 and formed with a key groove 46*d* to receive the screw 38*c* of the projection 38*a*. Further, the circular tubing section 46*a* has a screw thread formed in its outer periphery. Thus, the female connector 46 has a bore to engage with the projection 38*a* of the male connector.

Similar to the holder 40*a*, the holder 48*a* is a flanged circular tubing member for holding centrally therein the optical fiber FBib held by a cylindrical ferrule 49. The optical fiber FBib held by the ferrule 49 is held by the holder 48*a* such that its end face is spaced a given distance from the flanged end face of the holder 48*a*. The holder 48*a* is attached, directed outwardly, to the periphery of the central aperture 46*b* of the discal section 46*c* such that the central optical axis of the optical fiber FBib held by the holder 48*a* is located substantially at the center of the central aperture 46*c* of the optical fiber FBib.

The ferrule 49 having the optical fiber FBib inserted therein at the core has a function to hold and protect the optical fiber FBib and may, as with the ferrule 49, typically be a zirconia ferrule or a metal ferrule formed of a metal such as nickel alloy.

The holder 48*b* is, as is the holder 40*b*, a flanged circular tubing member for holding the collimating lens 50, and its flange section is attached to the flange section of the holder 48*a* such that the center of the forward end face of the optical fiber FBib and the center of the collimating lens 50 are spaced from each other on the optical axis thereof by a given distance, specifically by the focal distance of the collimating lens 50.

Note that the central axis of the optical fiber FBib and the center of the collimating lens 50 are provided in an offset positional relationship permitting horizontal emission of light beam.

The optical fiber FBib guides the light transmitted from the optical fiber FBia and, depending upon the position in which the optical connector 34 is disposed, guides and transmits light to the optical fiber FBia. The forward end face of the optical fiber FBib and the forward end face of the ferrule 49 having the optical fiber FBib inserted therein at the core are inclined end faces forming an identical plane inclined a given angle with respect to the plane perpendicular to the optical axis of the optical fiber FBib.

The collimating lens 50 focuses the light collimated by the collimating lens 42, allows the focused light to enter the optical fiber FBib, and, depending upon the position in which the optical connector 34 is disposed, further collimates the light emitted from the tip of the optical fiber FBib, allowing the thus collimated light to enter the collimating lens 42. The forward end face of the optical fiber FBib and the collimating lens 50 are positioned such that the center of the inclined end face of the optical fiber FBib and the center of the collimating lens 50 are spaced from each other on the optical axis by a distance equal to the focal distance of the collimating lens 50.

The fastener screw 52 is a cylindrical member for fastening the male connector 38 and the female connector 46 and comprises a circular tubing section 52*a* opening on the side thereof closer to the female connector 46 and a discal section 52*c* having a central aperture 52*b* on the side closer to the male connector 38. The circular tubing section 52*a* has a screw thread formed in its inner periphery that engages with the screw thread formed in the outer periphery of the circular tubing section 46*a* of the female connector 46. The inner periphery of the fastener screw 52*c* engages with the screw thread of the female connector 46, and the discal section 52*c* supports the flange 38*b* of the male connector 38 from the bottom side (i.e., from the side closer to the optical fiber PBia).

The optical connector according to the invention is preferably composed such that the holder unit 35 and the mounting unit 36 can be detached and that the optical fiber FBia and the optical fiber FBib can be detached.

The optical connector 34 according to this embodiment is composed such that the fastener screw 52 can be removed from the female connector 46 by turning the fastener screw 52, and the mounting unit 36 can be removed from the holder unit 35 by separating the male connector 36 from the female connector 46.

Further, such a configuration whereby the holder unit 35 and the mounting unit 36 of the connector 34 are separable permits replacements on a component part basis. For example, the optical probe can be replaced with one having a required length; the light source or the optical path length adjustor can also be replaced.

Further, since the optical fibers FBia and FBib have the collimating lenses 42 and 50 fitted at their respective forward ends, accidental damage or break of the forward ends of the optical fibers FBia and FBib can be prevented.

Preferably, the male connector and the female connector are attached by a snap-fit type lock. A snap-fit type lock provides an easy attachment and detachment and an assured lock minimizing the chance of displacement as compared with a more simply devised engagement.

Further, when the male connector has the screw that serves as a key and the female connector has the key groove to provide the positioning mechanism of the male connector and the female connector, the forward end faces of the optical fiber FBia and the optical fiber FBib can be placed in a constant positional relationship, that is, the forward end face of the optical fiber FBia and the forward end face of the optical fiber FBib can be placed in a symmetrical position even when replacement is made.

The contact surface between the male connector and the female connector formed into a tapered shape permits positioning of the male connector and the female connector with an increased precision and keeps the distance between the collimating lenses constant.

Still further, such a precise positioning allows the male connector and the female connector to be positioned with precision and therefore permits easy positioning of the optical fiber FBia and the optical fiber FBib in a symmetrical disposition even when the male connector and the female connector are given a compatibility (that is, when a different female connector is attached).

Preferably, knurls are formed on the contact surfaces of the male connector and the female connector, i.e., the outer periphery of the projection of the male connector and the inner periphery of the bore (circular tubing section) of the female connector.

Knurls formed on the contact surfaces of the male connector and the female connector prevents formation of a space between the contact surfaces of the male connector and the female connector when fitting one with the other and prevents entry of foreign matter between the collimating lenses.

According to the optical connector 34 of the invention, the forward end faces of the optical fibers FBia and FBib are inclined each a given angle to reduce the attenuation of the light transmitted from the optical fiber FBia to the optical fiber FBib or the light transmitted from the optical fiber FBib to the optical fiber FBia and prevent light reflected by the end faces of optical fibers from combining with transmitted light for improved signal-to-noise ratio of the light transmitted through the optical fiber FBia and the optical fiber FBib. FIG. 4 is a schematic view illustrating the positional relationship between the optical transmission system comprising the optical fiber FBia and the collimating lens 42 and the optical transmission system comprising the optical fiber FBib and the collimating lens 50.

The optical transmission system comprising the optical fiber FBia and the collimating lens 42 and the optical transmission system comprising the optical fiber FBib and the collimating lens 50 illustrated in FIG. 4 are disposed so as to be symmetric to a plane perpendicular to the optical axis (to be more precise, a plane passing through the midpoint between the optical fiber FBia and the optical fiber FBib and perpendicular to the optical axis), that is, disposed with line symmetry.

Specifically, as illustrated in FIG. 4, let $\theta_1$ be the inclination angle of the inclined end face of the optical fiber FBia with respect to a plane perpendicular to the central axis thereof, $n_1$ the refractive index of the optical fiber FBia, $n_3$ the refractive index of a medium between the optical fibers FBib and FBia that propagates the light excluding the collimating lenses 42 and 50, and $\theta_3$ the angle (refracting angle) of the light traveling inside the optical fiber FBia in the direction parallel to the central axis thereof and refracted at the interface between the inclined end face of the optical fiber FBia and the medium with respect to the normal line to the inclined end face, and suppose that the distance along the optical axis between the center of the inclined end face of the optical fiber FBia and the center of the collimating lens 42 is equal to a focal distance f1 of the collimating lens 42 on the assumption that the collimating lens 42 is a thin sheet lens.

Likewise, as illustrated in FIG. 4, let $\theta_2$ be the inclination angle of the inclined forward end face of the optical fiber FBib with respect to the plane perpendicular to the central axis thereof, $n_2$ the refractive index of the optical fiber FBib, $n_3$ the refractive index of the above medium propagating the light, and $\theta_4$ the angle (refracting angle) of the light traveling inside the optical fiber FBib in the direction parallel to the central axis thereof and refracted at the interface between the inclined end face and the medium with respect to the normal line to the inclined end face, and suppose that the distance along the optical axis between the center of the inclined end face of the optical fiber FBib and the center of the collimating lens 50 is equal to a focal distance f2 of the collimating lens 50 on the assumption that the collimating lens 50 is a thin sheet lens.

Then, both transmission systems will share the refractive index ($n_1=n_2$), the inclination angle ($\theta_1=\theta_2$), the refracting angle ($\theta_3=\theta_4$), the focal distance (f1=f2), and the offset amount ($\delta_1=\delta_2$).

As described above, the disposition of the optical transmission system comprising the optical fiber FBia and the collimating lens 42 and the optical transmission system comprising the optical fiber FBib and the collimating lens 50 illustrated in FIG. 4 lessens the attenuation of the returning light L3 from the object under measurement to reduce white noise and improve the signal-to-noise ratio of the returning light L3.

Now, for example, in FIG. 4, let the refractive index $n_1$ of the optical fiber FBia be 1.5, its inclination angle $\theta_1$ be 8°, and the refractive index $n_3$ of the medium be 1.0 assuming that it is air. Then, the refracting angle $\theta_3$ is 12° from the following expression:

$$n_1 \times \sin \theta_1 = n_3 \times \sin \theta_3$$

The inventive optical connector is basically configured as described above.

Now, description will be made of the components of the optical tomographic imaging system 10 illustrated in FIG. 1 to which the optical connector 34 of the invention is applied.

As illustrated in FIG. 1, the light source unit 12 comprises a semiconductor optical amplifier 60, an optical splitter 62, a collimating lens 64, a diffraction grating element 66, an optical system 67, and a rotary polygon mirror 68 and emits laser beam La that is frequency-swept with a constant period.

The semiconductor optical amplifier (semiconductor gain medium) 60 emits feeble light upon application of drive current and amplifies incoming light. The semiconductor optical amplifier 60 is connected with an optical fiber FB10. More specifically, one end of the optical fiber FB10 is connected to a part of the semiconductor optical amplifier 60 at which light is emitted, whereas the other end of the optical fiber FB10 is connected to a part of the semiconductor optical amplifier 60 at which light enters. The light emitted from the semiconductor optical amplifier 60 is emitted to the optical fiber FB10 and re-enters the semiconductor optical amplifier 60.

Thus, the semiconductor optical amplifier 60 and the optical fiber FB10, forming an optical path loop, provide an optical resonator. Application of activating electric current to the semiconductor optical amplifier 60 causes a pulse laser beam to be generated.

The optical splitter 62 is provided on the optical path of the optical fiber FB10 and also connected with an optical fiber FB11. The optical splitter 62 directs part of the light guided through the optical fiber FB10 to the optical fiber FB11.

The collimating lens 64 is disposed at the other end of the optical fiber FB11, i.e., the end thereof not connected with the optical fiber FB10, and collimates the light emitted from the optical fiber FB11.

The diffraction grating element 66 is disposed with a given inclination angle on the optical path of the parallel light produced by the collimating lens 64. The diffraction grating element 66 disperses the parallel light emitted from the collimating lens 64.

The optical system 67 is disposed on the optical path of the light dispersed by the diffraction grating element 66. The optical system 67 comprises a plurality of lenses to refract the light dispersed by the diffraction grating element 66 and collimate the refracted light.

The polygon mirror 68 is disposed on the optical path of the parallel light produced by the optical system 67 to reflect the parallel light. The polygon mirror 68 is a rotary unit that turns at a constant speed in the RI direction indicated in FIG. 1. It has the shape of a regular octagon in a plane perpendicular to the axis of rotation thereof and comprises lateral planes (planes forming the sides of the octagon) irradiated with the parallel light each formed with a reflection surface for reflecting the light.

The polygon mirror 68 turns to vary the angle of the reflection surfaces with respect to the optical axis of the optical system 67.

The light emitted from the optical fiber FB11 passes through the collimating lens 64, the diffraction grating element 66, and the optical system 67-and is reflected by the polygon mirror 68. The reflected light passes through the optical system 67, the diffraction grating element 66, and the collimating lens 64 and enters the optical fiber FB11.

Since the angle of the reflection surfaces of the rotary polygon mirror 6B varies with respect to the optical path of the optical system 67 as described above, the angle at which the rotary polygon mirror 68 reflects the light varies with time. Accordingly, only the light having a particular frequency range among the light dispersed by the diffraction grating element 66 re-enters the optical fiber FB11. Thus, since the light having a particular frequency range entering the optical fiber FB11 is determined by the angle formed by the optical axis of the optical system 67 and the reflection surface of the rotary polygon mirror 68, the frequency range of the light entering the optical fiber FB11 varies with the angle formed by the optical axis of the optical system 67 and the reflection surface of the rotary polygon mirror 68.

The light having a particular frequency range allowed to enter the optical fiber FB11 is delivered through the optical coupler 62 to the optical fiber FB10 and combined with the light of the optical fiber FB10. Thus, the pulse laser beam guided to the optical fiber FB10 becomes a laser beam having a particular frequency range and this laser beam La having a particular frequency range is emitted to the optical fiber FB3.

Since the polygon mirror 68 is turning at a constant speed in the direction indicated by the arrow R1, the wavelength λ of the light re-entering the optical fiber FB11 varies with a constant period as time passes. Accordingly, the frequency of the laser beam La emitted to the optical fiber FB3 also varies with a constant period as time passes.

The light source unit 12 is configured as described above and emits the wavelength-swept laser light La to the optical fiber FB3.

The interferometer 14 comprises the splitter 25, the combiner 26, the circulators 27a, 27b, the optical path length adjustor 28, the polarization controllers 29a, 29b, and the interference light detector 20.

The splitter 25 is formed, for example, by a 2×2 optical fiber coupler and optically connected to the optical fiber FB3 (FB3b), the optical fiber FB4, and the optical fiber FB4'.

The splitter 25 splits the incoming light La delivered from the light source unit 12 through the optical fiber FB3 (FB3a and FB3b) into the measuring light L1 and the reference light L2, directing the measuring light L1 to the optical fiber FB4' and the reference light L2 to the optical fiber FB4.

The combiner 26 is formed, for example, by a 2×2 optical fiber coupler and optically connected to the optical fiber FB6, the optical fiber FB7, the optical fiber FB8 (FB8a), and the optical fiber FB9 (FB9a).

The combiner 26 combines the incoming reference light L2a delivered from the optical fiber FB6 and the incoming returning light delivered from the optical fiber FB7 to produce first interference light L4a and second interference light L4b, directing the first interference light L4a to the optical fiber FB8 and the second interference light L4b to the optical fiber FB9.

The optical circulator 27a is connected with the optical fibers FB4', FB5 (FB5a), and FB6, and transmits light guided through a given optical fiber to another given optical fiber. Specifically, the optical circulator 27a delivers the reference light L2 guided from the splitter 25 through the optical fiber FB4' to the optical path length adjuster 28 through the optical fiber FB5 and delivers the reference light L2a, which is guided through the optical fiber FB5 after being reflected in the optical path length adjuster 28, to the polarization controller 29a through the optical fiber FB6.

The optical circulator 27b is connected with the optical fibers FB4, FB2 (FB2a), and FB7, and transmits light guided through a given optical fiber to another given optical fiber. Specifically, the optical circulator 27b delivers the measuring light L1 guided from the splitter 25 through the optical fiber FB4 to the optical connecter 18 through the optical fiber FB2 and transmits the returning light L3 guided from the optical connecter 18 through the optical fiber FB2 to the polarization controller 29b through the optical fiber FB7.

The optical path length adjuster 28 is disposed on the emission side of the optical fiber FB5 from which the reference light L2 is emitted (i.e., at the end of the optical fiber FB5 opposite from the splitter 25).

The optical path length adjuster 28 comprises a first optical lens 80 for collimating the light emitted from the optical fiber FB5, a second optical lens 82 for focusing the light collimated by the first optical lens 80, a reflecting mirror 84 for reflecting the light focused by the second optical lens 82, a base 86 for supporting the second optical lens 82 and the reflecting mirror 84, and a mirror moving mechanism 88 for moving the base 86 in the direction parallel to the optical axis. The optical path length adjuster 28 adjusts the optical path length of the reference light L2, L2a by varying the distance between the first optical lens 80 and the second optical lens 82.

The first optical lens 80 collimates the reference light L2 emitted from the core of the optical fiber FB5 and focuses the reference light L2 reflected by the reflecting mirror 84 onto the core of the optical fiber FB5.

The second optical lens 82 focuses the reference light L2 collimated by the first optical lens 80 onto the reflecting mirror 84 and collimates the reference light L2a reflected by the reflecting mirror 84. Thus, the first optical lens 80 and the second optical lens 82 form a confocal optical system.

The reflecting mirror 84 is disposed at the focal point of the light focused by the second optical lens 82 and reflects the reference light L2 focused by the second optical lens 82.

Thus, the reference light L2 emitted from the optical fiber FB5 is collimated by the first optical lens 80 and focused by the second optical lens 82 onto the reflecting mirror 84. Subsequently, the reference light L2a reflected by the reflecting mirror 84 is collimated by the second optical lens 82 and focused by the first optical lens 80 onto the core of the optical fiber FB5.

The base 86 fixedly holds the second optical lens 82 and the reflecting mirror 84 in position while the mirror moving mechanism 88 moves the base 86 in the direction of the optical axis of the first optical lens 80 (the direction indicated by the arrow A in FIG. 1).

The movement of the base 86 effected by the mirror moving mechanism 88 in the direction indicated by the arrow A changes the distance between the first optical lens 80 and the second optical lens 82, permitting the adjustment of the optical path length of the reference light L2, L2a.

The detector 30a is provided on the optical fiber FB8 (FB8a) to detect the light intensity of the first interference light L4a guided through the optical fiber FB8.

The detector 30b is provided in the optical fiber FB9 (FB9a) to detect the light intensity of the second interference light L4b guided through the optical fiber FB9.

The polarization controller 29a is optically connected with the optical fiber FB6 and rotates the polarization direction of the reference light L2a. The polarization controller 29b is optically connected with the optical fiber FB7 and rotates the polarization direction of the returning light L3.

The polarization controllers 29a, 29b may be configured using known technology such as is disclosed, for example, in JP 2001-264246 A.

Sharper tomographic images can be obtained by adjusting the polarization direction with the polarization controllers 29a and 29b such that the polarization directions of the returning light L3 and the reference light L2 coincide as they are combined by the combiner 26.

The polarization controllers 29a and 29b preferably permit operation thereof by a medical person at the operation control.

The interference light detector 20 is connected with the optical fibers FB8 and FB9, respectively, and detects or generates the interference signal from the difference between the first interference light L4a passed through the first detector 30a and the second interference light L4b passed through the second detector 30b.

Specifically, the interference light detector 20 is formed of a detecting unit formed by, for example, a photodiode for detecting the interference light by photoelectric conversion and a differential amplifier for detecting the difference from the value detected by the detecting unit; the interference light detector 20 effects photoelectric conversion of the first interference light L4a and the second interference light L4b in the detecting unit, enters the detected value in the differential amplifier 73 and amplifies the difference in the differential amplifier 73 to produce the interference signal.

Thus, performing balance detection of the two beams of interference light, the first interference light L4a and the second interference light L4b, permits producing an amplified interference signal while removing the common-mode optical noise from the interference signal, which enables improvement of the image quality of the acquired tomographic image.

According to the detection results given by the detectors 30a and 30b, the interference light detector 20 adjusts the balance between the first interference light L4a and the second interference light L4b in the optical intensity with which detection is made.

Thus, adjusting the balance of the optical intensity between the first interference light L4a and the second interference light L4b according to the detection results given by the detectors 30a and 30b or, specifically, adjusting the optical intensity to 50:50 permits reducing the white noise component and increasing the signal-to-noise ratio.

The optical probe 16 is connected to the optical fiber FB2 through the rotary drive unit 18 such that the measuring light L1 is delivered from the optical fiber FB2 to the optical fiber FB1 through the rotary drive unit 18; the measuring light L1 is then further transmitted by the optical fiber FB1 to irradiate the object under measurement S and acquire the returning light L3 from the object under measurement S; and the returning light L3 thus acquired is transmitted by the optical fiber FB1 to the optical fiber FB2 through the rotary drive unit 18.

Figure 5:
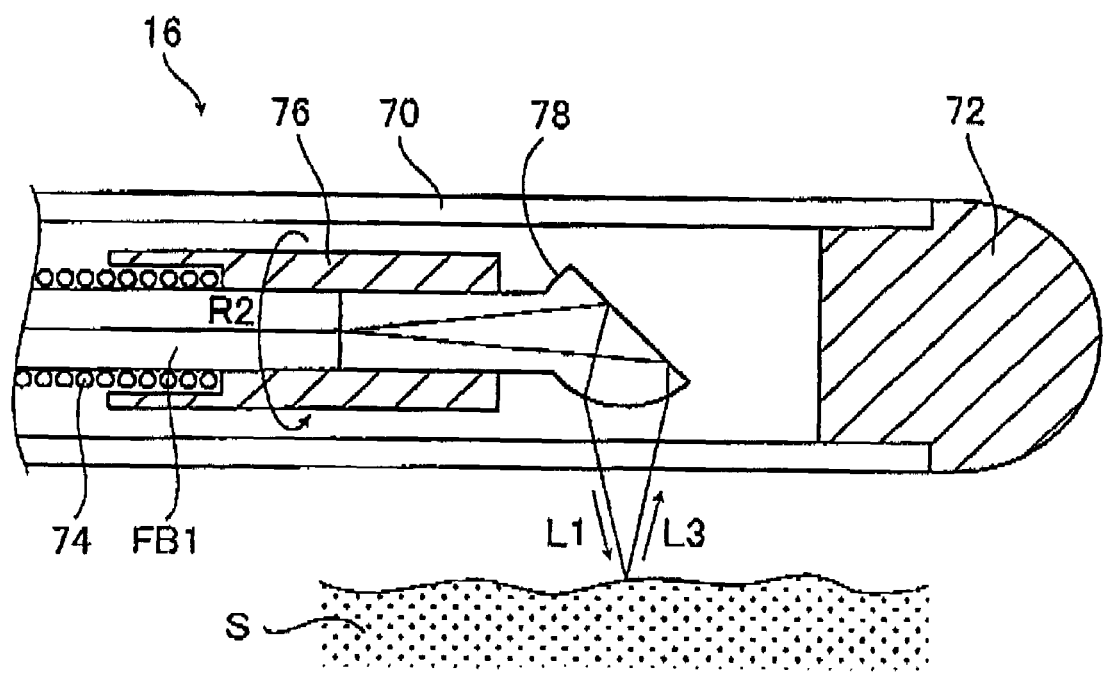
FIG. 5 is a partial, sectional view illustrating an embodiment of an optical probe of the optical tomographic imaging system of FIG. 1, with the tip of the optical probe shown enlarged.

As illustrated in FIG. 5, the optical probe 16 comprises a probe sheath 70, a cap 72, an optical fiber FB1, a spring 74, a holder member 76, and an optical lens 78.

The probe sheath 70 is a cylindrical member having a flexibility and formed of a material permitting transmission of the measuring light L1 and the returning light L3. The probe sheath 70 has at least part thereof close to its tip where the measuring light L1 and the returning light L3 pass the probe sheath 70 (ire., the end of the optical fiber FB1 opposite from the rotary drive unit 18, which will be referred to as the tip of the probe sheath 70 below) formed, throughout the circumference, of a material permitting transmission of light (transparent material).

The cap 72 is provided at the tip of the probe sheath 70 to close the tip of the probe sheath 70.

The optical fiber FB1 is a linear member encased in the probe sheath 70 along the length thereof; it guides the measuring light L1 delivered from the optical fiber FB2 through the rotary drive unit 18 to an optical lens 78 and guides the returning light L3 from the object under measurement S, which is acquired by the optical lens 78 by irradiating the object under measurement S with the measuring light L1, to the rotary drive unit 18, the returning light L3 then entering the optical fiber FB2.

The optical fiber FB1 and the optical fiber FB2 are connected by the rotary drive unit 18; they are optically connected such that the rotation of the optical fiber FB1 is not conveyed to the optical fiber FB2. The optical fiber FB1 is provided rotatably in relation to the probe sheath 70.

The spring 74 is secured to the periphery of the optical fiber FB1. The optical fiber FB1 and the spring 74 are connected to the rotary drive unit 18.

The optical lens 78 is disposed at the measuring end of the optical fiber FB1 (the end of the optical fiber FB1 opposite from the rotary drive unit 18) and has an end formed to have a substantially spherical shape to focus the measuring light L1 delivered from the optical fiber FB1 onto the object under measurement S.

The optical lens 78 irradiates the object under measurement S with the measuring light L1 delivered from the optical fiber FB1 and directs the returning light L3 from the object under measurement S to the optical fiber FB1.

The holder member 76 is disposed over the joint between the optical fiber FB1 and the optical lens 78 to secure the optical lens 78 to the end of the optical fiber FB1. The holder member 76 may secure the optical fiber FB1 and the optical lens 78 by any of the methods including but not limited to a method using an adhesive material to bond the holder member 76 to the optical fiber FB1 and the optical lens 78 and a method using a mechanical structure including bolts. The holder member 76, as with the ferrules 41 and 49 described earlier, may be any appropriate member such as a zirconia ferrule or a metal ferrule used for securing, holding and protection.

The rotary drive unit 18 is a rotary joint or the like, which rotatably holds the optical fiber FB1 with respect to the optical fiber FB2 and optically connects the optical fiber FB1 and the optical fiber FB2. The rotary drive unit 18 is connected with the optical fiber FB1 and the spring 74 such that the rotation of the optical fiber FB1 and the spring 74 causes the optical lens 78 to turn in relation to the probe sheath 11 in the direction indicated by the arrow R2. The rotary drive unit 18 has a rotary encoder (not shown) to detect the irradiation position of the measuring light L1 according to the position information (angular information) on the optical lens 78 based on the signal given by the rotary encoder. That is, the measuring position is determined by detecting the angle of the rotating optical lens 78 with respect to a reference position in the direction of rotation.

The optical probe 16 and the rotary drive unit 18 are configured as described above. As the rotary drive unit 18 turns the optical fiber FB1 and the spring 74 in the direction indicated by the arrow R2 in FIG. 4, the optical probe 16 irradiates the object under measurement S with the measuring light L1 emitted from the optical lens 78 by scanning in the direction indicated by the arrow R2 in FIG. 5 (in the circumferential direction of the probe sheath 70) and acquires the returning light L3.

Thus acquired is the returning light L3 for the whole circumference of the probe sheath 70 as it is reflected by the object under measurement S.

From the interference signal detected by; the interference light detector 20, the processor 22 detects the area where the optical probe 16 in the measuring position is in contact with the object under measurement S or, more precisely, the area where the surface of the probe sheath 70 may be considered to be in contact with the surface of the object under measurement S, and acquires a tomographic image from the interference signal detected by the interference light detector 20.

Figure 6:
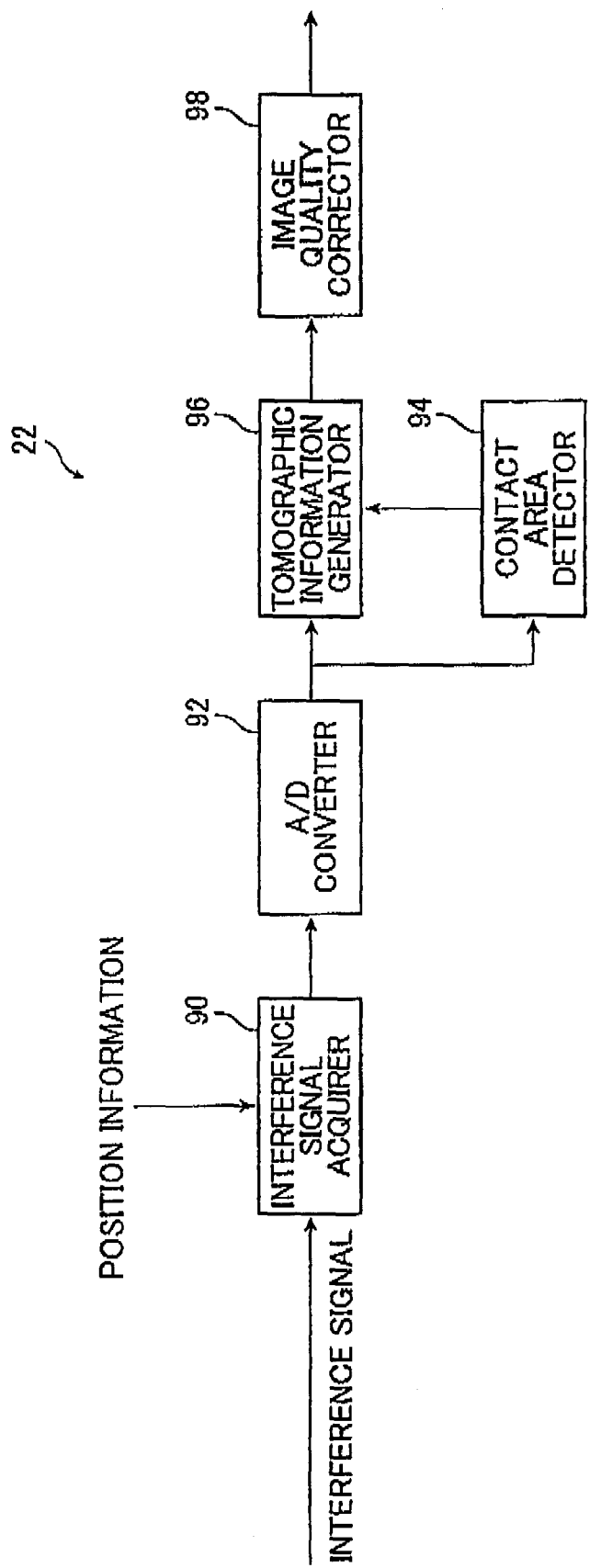
FIG. 6 is a block diagram schematically illustrating a configuration of an embodiment of the processor in the optical tomographic imaging system of FIG. 1.

As illustrated in FIG. 6, the processor 22 comprises an interference signal acquirer 90, an analog-to-digital converter 92, a contact area detector 94, a tomographic information generator 96, and an image quality corrector 98.

The interference signal acquirer 90 acquires the interference signal detected by the interference light detector 20 and acquires information on a measuring position detected by the rotary drive unit 18, more specifically, position information on the measuring position detected from the information on a position of the optical lens 78 in the rotating direction, and correlates the interference signal with the position information on the measuring position.

The interference signal correlated with the position information on the measuring position is sent to the analog-to-digital converter 92.

The analog-to-digital converter 92 converts to digital signal the interference signal produced from the interference signal acquirer 90 as analog signal correlated with the position information on the measuring position.

The interference signal now correlated with the position information on the measuring position and converted to digital signal is sent to the contact area detector 94 and the tomographic information generator 96.

The contact area detector 94 applies fast Fourier transform (FFT) to the interference signal now converted to digital signal by the analog-to-digital converter 92 to acquire the relationship between frequency component and intensity of the interference signal and associates the frequency component, which is now correlated with the intensity, with the depth direction (the direction in which the distance from the center of rotation increases) to acquire information on the relationship between depth direction and intensity. From the information on the relationship between depth direction and intensity, the contact area detector 94 detects the position on the surface of the probe sheath 70 at which the measuring light L1 is transmitted and the contact area between that position on the surface of the probe sheath 70 at which the measuring light L1 is transmitted and the object under measurement S.

Thus, information on the contact area between the probe sheath 70 and the object under measurement S is sent to the tomographic information generator 96.

The tomographic information generator 96 processes the information on the relationship between frequency component and intensity obtained by fast Fourier transform applied to the interference signal converted to digital signal by the analog-to-digital converter 92 to acquire a depthwise tomographic image.

The tomographic information generator 96 only acquires a tomographic image from the interference signal of the information on a position judged to be the contact area from among the contact area information sent from the contact area detector 94 and acquires no tomographic image from an interference signal of the information on a position representing an area other than the contact area, that is, performs no FFT or no image acquisition processing from the results obtained by application of FFT, performing instead a masking process.

Now, description will be briefly made on the generation of an image performed by the tomographic information generator 96.

Let S(1) be the optical intensity of interference fringes for each optical path length difference 1 of the various optical path length differences with which the returning light Lb from the respective depths in the object under measurement S interferes with the reference light L2 as the measuring light L1 irradiates the object under measurement S. Then, the optical intensity I(k) of the interference signal detected in the interference light detector 20 is expressed by an expression:

$$I(k) = \int S(1)[1 + \cos(k1)] dl$$

where k is the number of waves and 1 the optical path length difference. The above expression may be considered to represent an interferogram for a frequency range having the number of waves k=ω/c as a variable. Accordingly, applying fast Fourier transfer to the spectral interference fringes detected by the interference light detector 20 and determining the optical intensity S(1) of the interference light L4 in the tomographic information generator 96 yield information on the distance from the measurement starting position of the object under measurement S and reflection intensity information, thereby generating a tomographic image.

The image quality corrector 98 performs logarithmic conversion and radial conversion of the tomographic image generated by the tomographic information generator 96 to obtain a circular image centering about the center of rotation of the optical lens 78.

The image quality corrector 98 further performs sharpening processing, smoothing processing and the like on the tomographic image to correct the image quality.

The image quality corrector 98 sends the tomographic image with image quality corrected to the display 24.

The tomographic image may be sent at any appropriate timing; it may be sent to the display each time processing for one scan line is completed to effect rewrite each time one scan line is provided, or may be sent when processing for all the scan lines is completed (that is, when processing is completed to acquire an image as the optical lens has completed its one full rotation) to generate a circular tomographic image.

The display 24, which may be a CRT, a liquid crystal display device or the like, displays the tomographic image sent from the image quality corrector 98.

The operation control 32 comprises entry means such as a keyboard and a mouse, and control means for controlling various conditions according to the entered information and is connected to the processor 22 and the display 24. The operation control 32 performs, among others, entry, setting and change of thresholds, various processing conditions, etc. in the processor 22 and change of display settings in the display 24 according to the operator instructions entered at the entry means. The operation screen for the operation control 32 may be given on the display 24 or may be displayed on a separately provided monitor. The operation control 32 may be adapted to perform operation controls and settings of various conditions for the light source unit 12, the optical rotary adapter 18, the interference light detector 20, the optical path length adjuster 26 and the detectors 30a and 30b.

The optical tomographic imaging system 10 of the invention is basically configured as described above.

Next, the operations of the inventive optical tomographic imaging system 10 and the inventive optical connecter 18 will be described.

Description will be first made as to how the interference light and then the interference signal are acquired upon measuring the object under measurement S.

First, the mirror moving mechanism 82 is activated to move the base 86 in the direction indicated by the arrow A to adjust and set the optical path length such that the object under measurement S is positioned within a measurable range.

Subsequently, the light source unit 12 emits the laser beam La. The emitted laser beam La is split by the splitter 25 into the measuring light L1 and the reference light L2. The measuring light L1 is guided through the optical fiber FB4, the circulator 27b, the optical fiber FB2, the rotary drive unit 18, and the optical probe 16 (optical fiber FB1) to irradiate the object under measurement S.

At this time, the rotary drive unit 18 is rotating the optical fiber FB1 and the optical lens 78 in the optical probe 16 and therefore the object under measurement S such as a bodily cavity is irradiated with the measuring light L1 throughout the circumference thereof using the rotating optical lens 78. Meanwhile, the optical rotary adapter 18 detects information on the measuring position of the object under measurement S using a rotary encoder (not shown).

Subsequently, the light reflected at individual depth positions of the object under measurement S enters the optical probe 16 as the returning light L3. Since the rotary drive unit 18 is still rotating the optical fiber FB1 and the optical lens 78 inside the optical probe 16, the returning light L3 from the object under measurement S for the whole circumference of the object under measurement S enters the rotating optical-lens 78. This returning light L3 is delivered to the combiner 26 through the optical probe 16 (optical fiber FB1), the rotary drive unit 18, the optical fiber FB2, the circulator 27b and the polarization controller 29b.

Meanwhile, the reference light L2 is delivered through the optical fiber FB4′, the circulator 27a, and the optical fiber FB5 to the optical path length adjuster 28. The reference light L2a having its optical path length adjusted by the optical path length adjuster 28 is guided through the optical fiber FB5, the circulator 27a, the optical fiber FB6, and the polarization controller 29a back to the combiner 26.

The returning light L3 from the object under measurement S delivered to the combiner 26 is combined with the reference light L2a having its optical path length adjusted by the optical path length adjuster 28 to generate the first interference light L4a and the second interference light L4b.

The first interference light L4a and the second interference light L4b thus generated is detected as interference signal by the interference light detector 20.

As described earlier, the optical connector 34 is provided between the optical fiber FB2a and the optical fiber FB2b of the optical fiber FB2, between the optical fiber FB3a and the optical fiber FB3b of the optical fiber FB3, between the optical fiber FB5a and the optical fiber FB5b of the optical fiber FB5, between the optical fiber FB8a and the optical fiber FB8b of the optical fiber FB8, and between the optical fiber FB9a and the optical fiber FB9b of the optical fiber FB9, to optically connect the optical fibers FBia and the optical fibers FBib (i=2, 3, 5, 8 and 9).

The optical connector 34 provided on the optical fiber FB2 guides the measuring light L1 and the returning light L3, the optical connector 34 provided on the optical fiber FB3 guides the light La, the optical connector 34 provided on the optical fiber FB5 guides the reference light L2, L2a, the optical connector 34 provided on the optical fiber FB8 guides the interference light L4a, and the optical connector 34 provided on the optical fiber FB9 guides the. interference light L4b.

Now, the measuring light L1 and the returning light L3 transmitted through the optical connector 34 provided between the optical fiber FB2a and the optical fiber FB2b of the optical fiber FB2 will be described as a representative.

First, the measuring light L1 transmitted by the optical fiber FB2a and emitted from the inclined end face of the optical fiber FB2a enters the collimating lens 42 held by the holder 40b of the male connector 38 and, after collimation, enters the collimating lens 50 held by the holder 48b attached to the female connector 46. The measuring light L1 is then focused and allowed to hit the inclined end face of the optical fiber FB1 held by the holder 48a mounted to the female connector 46. The measuring light L1 is then transmitted into the optical fiber FB2b and delivered to the rotary drive 18 and the optical probe 16.

The returning light L3 from the object under measurement S is transmitted through the probe sheath 70 of the optical probe 16 to enter the rotating optical lens 78, then transmitted therefrom to the optical fiber FB1 in the optical probe 16 and the rotary drive unit 18 to enter the optical fiber FB2b.

In the optical connector 34, the returning light L3 emitted from the inclined end face of the optical fiber FB2b enters the collimating lens 50 held by the holder 48b of the mounting unit 36 to be collimated and enters the collimating lens 42 held by the holder 40b of the holder unit 35 to be focused. Then, the returning light L3 enters the inclined end face of the optical fiber FB2a held by the holder 40a of the holder unit 35, is transmitted through the optical fiber FB2a, and enters the circulator 27b.

At this time, since the light emitting end faces of the optical fiber FB2a and the optical fiber FB2b are symmetric to each other with respect to a plane perpendicular to the optical axis and inclined a given angle with respect to the optical axis, the light reflected upon the end faces is prevented from being guided along with the returning light L3, and the attenuation of the returning light L3 is minimized. Further, the white noise is reduced, and the signal-to-noise ratio of the returning light L3 is increased.

In each of the optical connectors disposed at the other positions, similarly, the light reflected upon the end faces is prevented from being guided along with the transmitted light, and the attenuation of the transmitted light is minimized. Further, the white noise is reduced, and the signal-to-noise ratio of the transmitted light is increased.

Then, the interference signal detected by the interference light detector 20 is sent to the processor 22.

In the processor 22, the interference signal acquirer 90 acquires the interference signal it receives as well as information on the measuring position detected by the rotary drive unit 18 to correlate the interference signal with the information on the measuring position.

Then, the analog-to-digital converter 92 converts the interference signal acquired by the interference signal acquirer 90 and correlated with the information on the measuring position from analog signal to digital signal. The interference signal now correlated with the information on the measuring position and converted to digital signal is sent from the analog-to-digital converter 92 to the contact area detector 94 and the tomographic information generator 96.

The contact area detector 94 detects the contact area of the probe sheath 70 and the object under measurement S, whereon the information on the detected contact area of the probe sheath 70 and the object under measurement S is sent to the tomographic information generator 96.

From the contact area information sent from the contact area detector 94, the tomographic information generator 96 processes the information on the relationship between frequency component and intensity obtained by applying FFT to the interference signal converted into digital signal by the analog-to-digital converter 92 only where the interference signal is correlated with the information on the position judged to be a contact area to acquire a depthwise tomographic information for the contact area. The tomographic image acquired by the tomographic information generator 96 is sent to the image quality corrector 98.

The image quality corrector 98 performs logarithmic conversion and radial conversion on the tomographic image generated by the tomographic information generator 96 to make it a circular tomographic image the center of which registers with the center of rotation of the optical lens 78, as well as sharpening processing and smoothing processing and the like to correct the image quality.

The tomographic image having the image quality corrected by the image quality corrector 98 is sent to the display 24.

The display 24 shows the tomographic image sent from the image quality corrector 98 as an image after image quality correction.

While the optical tomographic imaging system 10 described above uses SS-OCT (swept source-OCT) measuring method to detect the contact area with the object under measurement and thereby acquire a tomographic image of the object under measurement, the invention is not limited in this way and may use any other OCT measuring method. The other OCT measuring methods that may be used here include, for example, an SD-OCT (spectral domain-OCT) measuring method and a TD-OCT (time domain-OCT) measuring method.

In the optical tomographic imaging system 10, a tomographic image is acquired by detecting the contact area with the object under measurement, and therefore the tomographic image thus acquired can be suitably used for analysis or other purposes. Further, different image processing is performed in the contact area than is performed in the noncontact area, and hence the amount of information that needs to be processed can be reduced while maintaining the image quality of the contact area. However, the present invention is not limited thereto; a tomographic image may be acquired without detecting the contact area.

While the optical connector of the invention and the optical tomographic imaging system using the same have been described in detail by reference to various embodiments thereof, the present invention is not limited in any manner to these embodiments, and various improvements and modifications may be made without departing from the spirit of the invention.

For example, while the holder unit and the mounting unit of the optical connector are provided each in a one-piece configuration in the above embodiment, any other configuration may be used, provided that the optical transmission system located on the side closer to the holder unit and comprising the optical fiber located on the side closer to the holder unit and the collimating lens located on the side closer to the holder unit can be provided in a one-piece configuration and the optical transmission system located on the side closer to the mounting unit and comprising the optical fiber located on the side closer to the mounting unit and the collimating lens located on the side closer to the mounting unit can be provided in a one-piece configuration, that the optical transmission system located on the side closer to the holder unit can be supported with respect to the optical transmission system located on the side closer to the mounting unit, and that the end face of the optical fiber located on the side closer to the holder unit and the optical fiber located on the side closer to the mounting unit are symmetric with respect to a plane perpendicular to the optical axis to prevent the light reflected upon the end faces from being guided along with the primary light to be guided, minimize the attenuation of the returning light L3, reduce the white noise, and increase the signal-to-noise ratio of the transmitted light. For example, the component parts such as the discal section, the circular tubing section, and cylindrical sections of the male connector of the holder unit and the female connector of the mounting unit may be provided as separate component parts.

The manner in which the holder unit is connected to the mounting unit and a mechanism whereby they are connected are not limited specifically, and various manners and mechanisms may be used as appropriate. Preferably, fastener screws are used to fasten the holder unit and the mounting unit to ensure their connection, but the invention is not limited thereto; the connection may be achieved without fastener screws.

Further, while the optical fibers and the ferrules of the optical connector are disposed such that the axes of these members lie in a direction parallel to the optical axis in the above embodiment, the invention is not limited to such a configuration; the optical fibers and the ferrules may be disposed such that the axes of the members are inclined each a given angle with respect to the optical axis.

What is claimed is:

1. An optical connector used in an optical tomographic imaging system for acquiring an optical tomographic image of an object under measurement, the optical connector comprising:

a holder unit;

a first optical fiber fixedly supported by the holder unit and having on one end thereof an end face inclined a given angle with respect to a plane perpendicular to its optical axis;

a first collimating lens disposed at a given distance from the inclined end face of the first optical fiber;

a mounting unit supported with respect to the holder unit;

a second optical fiber fixedly attached to the mounting unit, disposed opposite the first collimating lens, and having an end face inclined a given angle with respect to a plane perpendicular to its optical axis; and a second collimating lens fixedly attached to the mounting unit and disposed between the first collimating lens and the second optical fiber with a given distance from the inclined end face of the second optical fiber, wherein an optical transmission system comprising the first optical fiber and the first collimating lens is disposed symmetric to an optical transmission system comprising the second optical fiber and the second collimating lens with respect to a plane perpendicular to an optical axis, wherein the first optical fiber and the second optical fiber are supported by respective ferrules and the ferrules have inclined end faces forming same planes as the inclined end faces of the first optical fiber and the second optical fiber, respectively, and wherein the mounting unit fixedly supporting the second optical fiber and the second collimating lens is detachable from the holder unit fixedly supporting the first optical fiber and the first collimating lens.

2. The optical connector according to claim 1,
wherein the holder unit has a cylindrical projection of which an outer periphery has a tapered shape growing smaller in diameter toward a forward end thereof, and
wherein the mounting unit has a cylindrical bore having a tapered inner periphery in contact with the outer periphery of the projection such that the bore of the mounting unit engages with the projection of the holder unit to support the mounting unit with respect to the holder unit.

3. The optical connector according to claim 1, further comprising a positioning mechanism for fixing a position of the mounting unit with respect to the holder unit in a circumferential direction about an optical axis and fixing a relative position of the inclined end faces of the first optical fiber and the second optical fiber in a circumferential direction about an optical axis.

4. The optical connector according to claim 3, wherein the positioning mechanism comprises a key and a key groove that is formed in at least one of the holder unit and the mounting unit.

5. An optical tomographic imaging system comprising:
a light source;
a splitter for splitting light emitted from the light source into measuring light and reference light;
an optical probe for guiding the measuring light to an object under measurement and guiding returning light from the object under measurement, the optical probe having a measuring unit disposed at a tip thereof for radiating the measuring light to the object under measurement and detecting the returning light;
a rotary drive unit for rotating the measuring unit of the optical probe;
a combiner for combining the returning light detected by the measuring unit of the optical probe with the reference light to generate interference light;
an interference light detector for detecting the interference light as interference signal;
a tomographic information generator for acquiring a tomographic image from the interference signal detected by the interference light detector; and
a plurality of connecting units for optically connecting the light source and the splitter, the splitter and the rotary drive unit, the rotary drive unit and the combiner, and the combiner and the interference light detector, respectively,
wherein at least one of the connecting units comprises a plurality of optical fibers and an optical connector of claim 1 for establishing a connection between one optical fiber with another optical fiber.

6. The optical tomographic imaging system according to claim 5, wherein the light source emits light with a wavelength thereof swept with a constant period.

* * * * *